(12) United States Patent
Hijlkema et al.

(10) Patent No.: US 6,858,034 B1
(45) Date of Patent: Feb. 22, 2005

(54) STENT DELIVERY SYSTEM FOR PREVENTION OF KINKING, AND METHOD OF LOADING AND USING SAME

(75) Inventors: Lukas J. Hijlkema, Galway (IE); Fionnan Friel, Galway (IE); Michael McMahon, Limerick (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/573,273

(22) Filed: May 18, 2000

Related U.S. Application Data
(60) Provisional application No. 60/134,971, filed on May 20, 1999.

(51) Int. Cl.[7] .................................................. A61F 11/00
(52) U.S. Cl. ...................................... 606/108; 623/1.11
(58) Field of Search ................................ 606/108, 191, 606/198, 151, 192, 190; 623/1.11, 1.12

(56) References Cited

U.S. PATENT DOCUMENTS

| | | | |
|---|---|---|---|
| 4,950,227 A | 8/1990 | Savin et al. ..................... 604/8 |
| 5,026,377 A | 6/1991 | Burton et al. ................ 606/108 |
| 5,201,757 A | 4/1993 | Heyn et al. .................. 606/198 |
| 5,201,901 A | 4/1993 | Harada et al. ............... 606/198 |
| 5,480,423 A | 1/1996 | Ravenscroft et al. ........... 623/1 |
| 5,484,444 A | 1/1996 | Braunschweiler et al. .. 606/198 |
| 5,520,645 A | * 5/1996 | Imran et al. ................. 606/194 |
| 5,562,726 A | 10/1996 | Chuter ........................... 623/1 |
| 5,591,222 A | 1/1997 | Susawa et al. .................. 623/1 |
| 5,609,627 A | 3/1997 | Goicoechea et al. ............ 623/1 |
| 5,683,451 A | 11/1997 | Lenker et al. ............... 606/198 |
| 5,702,418 A | 12/1997 | Ravenscroft ................ 606/198 |
| 5,709,703 A | 1/1998 | Lukic et al. .................... 623/1 |
| 5,749,921 A | 5/1998 | Lenker et al. .................. 623/1 |
| 5,755,777 A | 5/1998 | Chuter ........................ 606/180 |
| 5,824,040 A | * 10/1998 | Cox et al. .................... 606/194 |
| 5,824,041 A | * 10/1998 | Lenker et al. ............... 606/195 |
| 5,843,167 A | 12/1998 | Dwyer et al. .................. 604/8 |
| 5,902,334 A | 5/1999 | Dwyer et al. |
| 5,968,068 A | * 10/1999 | Dehdashtian et al. .. 604/164.08 |
| 5,989,280 A | * 11/1999 | Euteneuer et al. ............ 623/1.1 |
| 6,110,191 A | * 8/2000 | Dehdashtian et al. .... 604/96.01 |
| 6,302,906 B1 | * 10/2001 | Goicoechea et al. ....... 623/1.11 |
| 6,319,275 B1 | * 11/2001 | Lashinski et al. .......... 623/1.11 |
| 6,500,202 B1 | 12/2002 | Shaolian et al. |

FOREIGN PATENT DOCUMENTS

| | | | |
|---|---|---|---|
| EP | 0 775 470 | 5/1997 | |
| EP | 0775470 | * 5/1997 | ............. A61F/2/06 |
| EP | 0 834 293 | 4/1998 | |
| WO | WO 95/33422 | 12/1995 | |
| WO | WO 98/53761 | 12/1998 | |

OTHER PUBLICATIONS

U.S. Appl. No. 09/574,418, filed May 19, 2000, DiMatteo et al.

* cited by examiner

Primary Examiner—Julian W. Woo
Assistant Examiner—Victor X Nguyen
(74) Attorney, Agent, or Firm—RatnerPrestia

(57) ABSTRACT

A stent delivery system adapted to deliver a compressed stent to a distal deployment location inside a body lumen from a proximal access location outside the body lumen. The system houses a compressed stent and includes a pusher and a catheter tip attached to a central core slideably disposed within the pusher. At least one of the pusher distal end and catheter tip proximal end comprises a docking section adapted to releasably engage a limited length of one end of the compressed stent. The docking section may comprise a pocket having a flared end rim that is radially biased outward and adapted to be inwardly compressed to grip the stent end when the docking section is loaded in an outer sheath. Other docking section configurations are also disclosed, such as an insert within the stent, an annular pocket, and/or a set of fingers that grip the stent. A docking pusher and a docking catheter tip having such docking sections are disclosed, as are methods for loading and deploying a stent with a stent delivery system as described herein.

36 Claims, 3 Drawing Sheets

STENT DELIVERY SYSTEM FOR PREVENTION OF KINKING, AND METHOD OF LOADING AND USING SAME

CROSS-REFERENCE TO RELATED APPLICATIONS

This application claims priority based upon U.S. Provisional Application Ser. No. 60/134,971, filed on May 20, 1999.

TECHNICAL FIELD

The present invention relates generally to endoluminal grafts or "stents" and, more specifically, to stent delivery systems or 'introducers'.

BACKGROUND OF THE INVENTION

A stent is an elongated device used to support an intaaluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft. As used herein, however, the term "stent" is a shorthand reference referring to a covered or uncovered such stent.

A stent may be used, for example, to treat a vascular aneurysm by removing the pressure on a weakened part of an artery so as to reduce the risk of rupture. Typically, an intraluminal stent is implanted in a blood vessel at the site of a stenosis or aneurysm endoluminally, i.e. by so-called 'minimally invasive techniques' in which the stent, restrained in a radially compressed configuration by a sheath or catheter, is delivered by a stent deployment system or 'introducer' to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter in the vessel into the deployment location, and the introducer is withdrawn. Stent expansion may be effected by spring elasticity, balloon expansion, or by the self-expansion of a thermally or stress-induced return of a memory material to a preconditioned expanded configuration.

Refering now to FIGS. 1A and 1B, there is shown a prior art, pre-loaded stent delivery system 10 for housing and deploying a compressed stent 14. Stent delivery system 10 comprises an outer sheath 12 and a conventional pusher or stabilizer 16 loaded proximal to the stent. As used herein, the term "proximal" refers to the end closer to an access location outside the body whereas "distal" refers to the farther from, the access location. Delivery system 10 also typically comprises a catheter tip 20 at the distal end and a pusher handle 25 located at the proximal end outside the body lumen. The catheter tip may be attached to central core 23 that runs through central lumen 22 within pusher 16. Central core 23 may guide the delivery system through the body lumen over a guidewire (not shown) to the area to be repaired, or may be adapted for inflating a balloon (if applicable), and/or for flushing the system. The delivery system may additionally have radiopaque markers at selected locations therein to be used for fluoroscopic guidance of the system through the body lumen.

To deploy stent 14, delivery system 10 is threaded through the body lumen to the desired location for stent deployment. Outer sheath 12 is then retracted, and pusher 16 acts as a stabilizer to keep stent 14 from retracting with the sheath. As outer sheath 12 retracts, stent 14 is exposed and expands into place against the body lumen to be repaired. The stent may be a self-expanding stent, such as a stent made of shape-memory nitinol (nickel-titanium) wire as are well-known in the art, or the stent may require inflation of a balloon to expand it against the walls of the body lumen, as is also well-known in the art.

Regardless of the type of stent or delivery system, the portion of delivery system 10 that houses compressed stent 14 typically has increased mass and rigidity as compared to the rest of delivery system 10. Thus, referring now to FIG. 2, when introducing delivery system 10 through tortuous anatomy, kinking of the delivery system may occur in region 17 of the system where pusher 16 and stent 14 interface, due to the rigidity of both the stent and the pusher. Kinking along kink angle "a" may develop as a result of the rigidity of compressed stent 14, whereas kinking along kink angle "b" may develop as a result of the rigidity of pusher 16. The resulting kink angle a+b is therefore dependent upon the material properties of both the compressed stent 14 and pusher 16. Similar kinking may also occur in region 18 where stent 14 and tip 20 interface.

Such kinking may prevent or hamper proper deployment of stent 14 because creases 15 that develop where sheath 12 is bent may prevent retraction of the sheath. Such creases 15 present a problem not only where stent 14 is intended for deployment in the tortuous portion of the body lumen, but also may persist even after the delivery system 10 is ultimately navigated past the tortuous portion of the lumen to a remote deployment site. Also, the discontinuity of the contact surface between stent 14 and pusher 16 could lead to an improper or inaccurate deployment of the stent. Where kinking causes such creases 15 in sheath 12 that prevent deployment, delivery system 10 must be retracted from the body and discarded, and the introduction process must start again with a new introducer. Thus, there is a need in the art to prevent such kinking in stent delivery systems.

SUMMARY OF THE INVENTION

The present invention provides a stent delivery system adapted to deliver a compressed stent to a distal deployment location inside a body lumen from a proximal access location outside the body lumen. The stent delivery system comprises at least one docking section defining a pocket adapted to releasably contain a limited length of one end of the compressed stent. In one embodiment, the stent delivery system houses a compressed stent having a proximal end and a distal end and comprises a pusher having a distal end located adjacent the stent proximal end and a catheter tip having a proximal end located adjacent the stent distal end and attached to a central core slideably disposed within the pusher. At least one of the pusher distal end and catheter tip proximal end comprises a docking section, which is adapted to releasably engage a limited length of one end of the compressed stent. The stent delivery system may further comprise an outer sheath overlying each docking section, the compressed stent, and the pusher.

The docking section may comprise a pocket adapted to contain the stent end inserted therein, including an annular pocket having an inner wall and an outer wall, or may be an axially-extending engagement surface which extends inside a short axial length of the stent. The docking section may comprise a set of fingers, such as an inner set of fingers that extend inside a short axial length of the stent, an outer set of fingers that extend over a short axial length of the stent, or a combination thereof forming an annular region between the inner and outer sets of fingers. The delivery system may comprise a pusher having a docking section biased radially outward and a catheter tip having a non-radially-biased outward docking section.

In one embodiment, the docking section pocket has a fed end rim that is biased radially outward and adapted to be radially inwardly compressed to grip the stent end when the docking section is loaded in the outer sheath. Such a docking section generally has a bottle-neck geometry when the flared end rim is compressed, and may pinch the stent inward against the central core in the compressed state.

The invention also comprises a pusher comprising a distal end having a docking section having a pocket therein adapted to releasably contain a limited length of a proximal end of the compressed stent inserted therein. The docking section may be integral to the pusher, or an attachment to the pusher. The invention further comprises a pusher comprising a distal end having a docking section that is biased radially outward relative to the compressed stent and adapted to releasably engage a limited length of a proximal end of the stent in pushing engagement therewith. Such a radially-biased-outward docking section may comprise a pocket adapted to contain the proximal end of the stent therein, or an insert adapted to be inserted within the stent proximal end.

The invention further comprises a catheter tip having a proximal end comprising a docking section adapted to releasably engage a limited length of a distal end of a compressed stent. The docking section may be integral to the catheter tip or an attachment thereto. The docking section of the catheter tip may have a flared end rim that is radially biased outward and adapted to be inwardly compressed into a bottle-neck shape to pinch the compressed stent inward against a central core upon insertion of the docking section within an outer sheath.

The invention further comprises a method for pre-loading the stent delivery system described above. The method comprises loading at least the compressed stent and pusher within the outer sheath, including releasably engaging a portion of the stent proximal end with a pusher docking section at the pusher distal end, or releasably engaging the stent distal end with a catheter tip docking section at the catheter tip proximal end, or both. The pusher docking section is either biased radially outward or defines a pocket in which the portion of the stent proximal end is nested. Where the system simply includes at least one docking section defining a pocket adapted to releasably contain a limited length of one end of the compressed stent, the method comprises loading the compressed stent about the central core between the catheter tip and the pusher, inserting one of the ends of the stent in the pocket, and enclosing at least the stent, central core, pusher, and each docking section within the outer sheath.

The invention further comprises a method for deploying a stent in a distal deployment location inside a body lumen from a proximal access location outside the body lumen. The method comprises introducing a pre-loaded stent delivery system as described above into the body lumen, navigating the stent delivery system to a desired location for deploying the stent, and retracting the outer sheath to deploy the stent from the outer sheath into the desired location and to release the stent from each docking section. Where the catheter tip has a docking section, the method may further comprise distally advancing the central core and the catheter tip attached thereto to further facilitate release of the stent from the catheter tip docking section.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

Figure 1A:
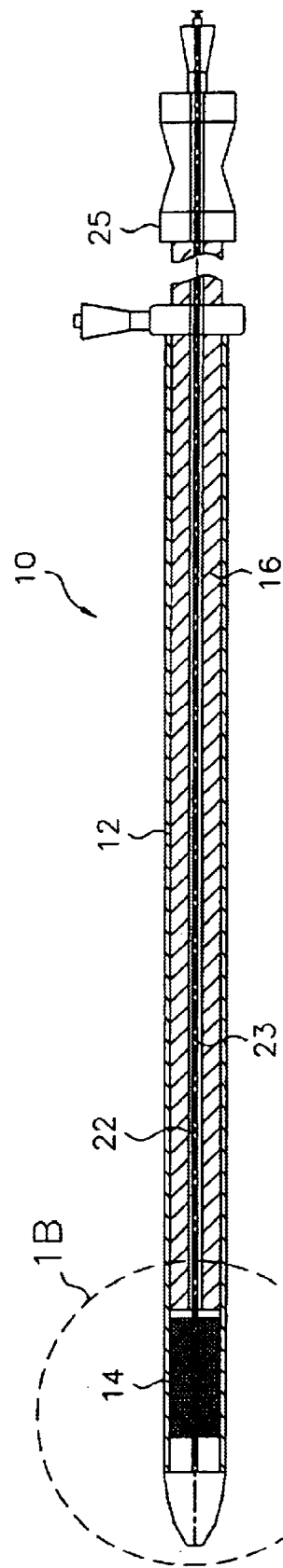
FIG. 1A is a longitudinal section schematic illustration of an exemplary stent delivery system of the prior art.
Figure 2:
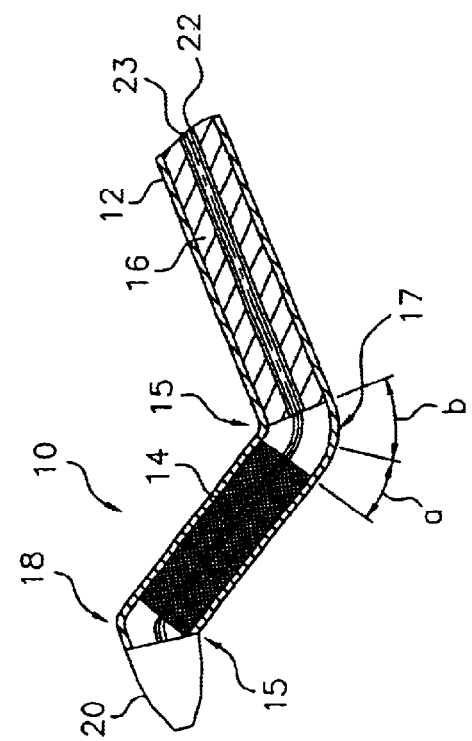
FIG. 2 is a longitudinal section schematic illustration of an exemplary stent delivery system of the prior art in a kinked state due to the varying rigidity along the system.
Figure 1B:
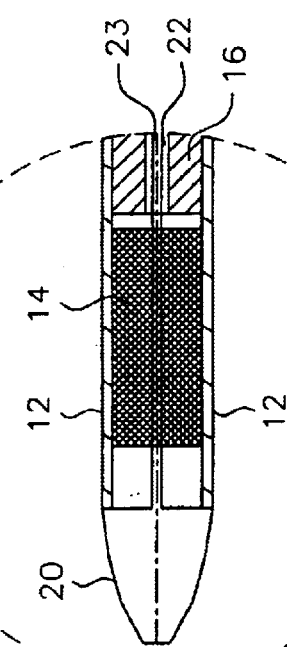
FIG. 1B is an enlarged portion of FIG. 1A.
Figure 3:
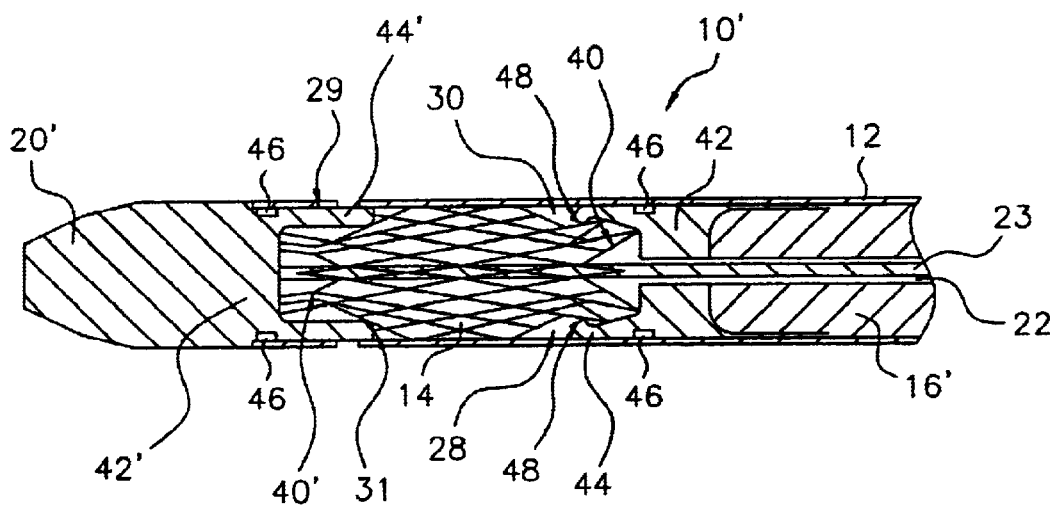
FIG. 3 is a longitudinal section schematic illustration of a portion of an exemplary stent delivery system of the present invention, showing the stent in a compressed state cradled in the docking section pockets of both the catheter tip and the pusher.
Figure 4:
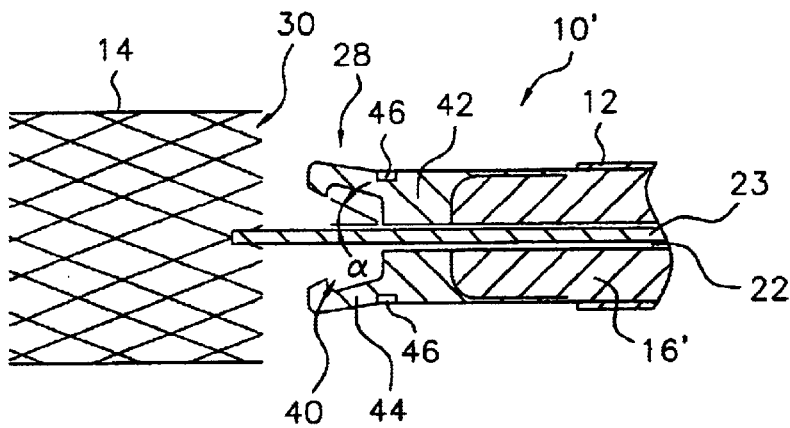
FIG. 4 is a longitudinal section schematic illustration of the pusher of FIG. 3 shown in a deployed state after retraction of the outer sheath.

Referring now to the drawing, wherein like reference numerals refer to like elements throughout, FIGS. 3–4 illustrate an exemplary stent delivery system 10' of the present invention, having an exemplary docking pusher 16' and docking catheter tip 20'. As shown in FIG. 3, stent delivery system 10' comprises an outer sheath 12, central lumen 22, and central core 23, similar to delivery systems known in the art. As used herein, the term "system" shall encompass both a completed assembly which is capable of deploying a stent or a subassembly which is capable of deploying a stent when combined with other components. Docking pusher 16' and catheter tip 20', however, comprise docking sections 42 and 42' respectively, each docking section having a pocket 40 and 40', respectively. Docking section 42 located at pusher distal end 28 is adapted to hold proximal end 30 of compressed stent 14, whereas docking section 42 located at catheter tip proximal end 29 is adapted to hold distal end 31 of compressed stent 14. Docking section 42 or 42' may be a discrete section connected to, respectively, pusher 16' or catheter tip 20', as shown in FIGS. 3 and 4 with respect to pusher 16', or may be a hollowed section integral to the rest of the pusher or catheter tip, as shown in the figures with respect to catheter tip 20'. Other docking section configurations or means for engaging the compressed stent end with the pusher or catheter tip may also be used, as described herein later.

The term "pusher" is used herein throughout, although such device may also be referred to in the art as a "stabilizer", because the method of deploying the stent may not actually comprise "pushing" the stent out of the sheath, but rather "stabilizing" the stent (holding it in place and preventing it from moving) while the outer sheath is retracted. Thus, use of the term "pusher" herein refers to such a device adapted for any method of deploying known in the art, including as a stabilizer, and the term "pusher" is not intended as a limitation thereof.

Docking pusher 16' and docking catheter tip 20' overcome kinking in the body lumen because a certain amount of compressed stent 14 is actually docked or cradled inside pocket 40 or 40', creating a smooth transition between the stent and the pusher or catheter tip. The pusher and stent and/or catheter tip and stent in such docked configurations thus move together at their respective interface points while navigating the tortuous anatomy of the body lumen, by minimizing any area of weakened rigidity to prevent kinks.

In addition, as long as rim 44 of docking section 42 in pusher 16' grips stent 14, the stent may be "recaptured" or "recovered" even once it has been partially deployed. For instance, if a medical professional determines that a partially deployed stent 14 needs to be repositioned, pusher 16' may be pulled back within sheath 12 or the sheath advanced to recover the partially deployed stent. Then, the deployment process can start over. Other embodiments having other means for releasably engaging the stent may offer similar recapture capabilities.

Also, because of the docked arrangement between stent 14 and pusher 16', the stent may be rotated, pushed, or pulled both before and during deployment, unlike with conventional deployment systems where the pusher can only transmit force in a pushing direction. For example, where the stent architecture has a particular feature intended for alignment with a particular part of the body lumen, such as a particularly flexible portion of the stent to be aligned with a tortuous portion of the body lumen, the stent can be rotated, pushed, or pulled to effect this alignment. Additionally, in the configuration shown in FIG. 3 where docking section 42 pinches stent 14 against central core 23, creating friction, there is less undesired movement of the stent inside the delivery system as compared to non-docked prior configurations. Additionally, the use of a docking section in the catheter tip may facilitate placement of the distal end of the stent in a predetermined location.

As shown in FIG. 3, stent 14 is held within pocket 40 of docking section 42 of pusher 16' and pinched inwardly by end rim 44. When compressed within sheath 12, docking section 42 has a bottleneck shape created by inward protrusions 48 of end rim 44 that define a neck with a smaller diameter than the remainder of pocket 40, as shown in FIG. 3. End rim 44 of docking section 42 thus has a normal radial bias outward that is compressed and confined within the walls of sheath 12 during introduction to the body. As shown in FIG. 4, once the target zone has been reached, outer sheath 12 is retracted. When sheath 12 is retracted beyond end rim 44 of docking section 42, rim 44 springs open into an outwardly flared configuration and releases proximal end 30 of stent 14. Accordingly, docking section 42 may comprise any material, such as stainless steel, that provides flared end rim 44 with the requisite "springiness" to pinch inward when compressed and to spring open when the sheath is retracted. Although illustrated with respect to the pusher docking section 42 in FIG. 4, this outwardly-flared configuration may also be applicable to catheter tip docking section 42'; however, as shown in FIG. 3, a non-outwardly-biased, cylindrical configuration is preferred, as described below.

Instead of having a bottleneck shape when compressed within sheath 12 and radially flared and biased outward when not housed within the sheath, end rim 44' of docking section 42' in catheter tip 20' is cylindrical in shape and capable of holding stent 14 within pocket 40' merely by frictional engagement. Prior to retraction of sheath 12 to deploy stent 14, central core 23 and tip 20' attached thereto may, in some cases, need to be advanced distally so that the stent disengages from the pocket 40'. Such a non-radially-biased pocket may also be provided on docking section 42 of pusher 16'. In such case, stent 14 may be partially deployed and anchored into the walls of a body lumen so that the stent has sufficient frictional resistance against the body lumen to enable pusher 16' to be retracted to disengage the stent from within the non-flared pocket without dislocating the stent.

The step of advancing catheter tip 20' prior to retraction of sheath 12 may also be performed to facilitate stent delivery even where docking section 42' includes a radially-biased end rim (not shown). Such a radially-biased end rim on catheter tip 20', however, may present difficulty in preparing delivery system 10' for retraction from the body after deployment unless there is some mechanism to re-compress the end rim back inside sheath 12. Without such re-compression of the radially-biased end rim back inside the sheath, such as is possible with respect to pusher 16' merely by retracting the pusher to pull end rim 44 back inside sheath 12, the radially-biased end rim may protrude from the streamlined shape of the delivery system at the catheter end during retraction and provide a catching point that may damage the body lumen. Thus, a non-radially-biased end rim 44' is preferred for catheter tip 20'.

Docking section 42 may include a radiopaque marker 46, to provide increased radiographic "vision" of the pusher end, and when combined with a similar marker (not shown) on the proximal end of stent 14, to visualize relative movement of pusher and stent as stent 14 disengages from pusher 16'. Similar markers 46 may also be provided for similar purposes on the catheter tip docking section 42' and on the stent distal end (not shown). "Radiopaque marker" as used herein encompasses any discrete area of different radiopacity as compared to a surrounding area.

Pusher docking sections, catheter tip docking sections, stent delivery systems, and methods incorporating such pushers and/or catheter tips may take a wide variety of forms other than that described specifically above. A particular stent delivery system may include only a pusher docking section, only a catheter tip docking section, or both. The essence of any such docking section is that it releasably engages an end of the stent over some axial length in a manner whereby that engagement is releasable upon stent deployment. The term "releasably engaging" denotes that the engagement between the docking section and the stent is not permanent, but rather is releasable in the sense that the stent is released from the docking section when the outer sheath is retracted or when the pusher or catheter tip is advanced or retracted away from the stent. The pusher docking section is either biased radially outward or defines a pocket in which the portion of the stent proximal end is nested.

The length of the stent engaged by the docking section of this invention should be sufficiently long, taking into account the stent diameter and flexibility as well as the tortuosity of the lumen to be traversed during its deployment, to maintain a pushing engagement notwithstanding the tortuosity for which the stent is designed. Such pushing engagement enables transmission of a pushing force applied thereto, such as from the pusher to the stent, or from the stent to the catheter tip. The length of the stent engaged by the docking section should be sufficiently short, however, and/or the angle of radial flare a (as shown in FIG. 4) sufficiently great, so as to facilitate reliable release of stent 14 when sheath 12 is retracted. The dimensions and mechanical features of individual docking section designs may be readily determinable by those skilled in the art.

In particular, the docking section may comprise an axially-extending engagement surface which extends over a short axial length of the stent either on the interior or exterior thereof. Such surface may define the interior of pocket 40 previously described and shown in FIGS. 3 and 4, or an insert adapted to be inserted within the stent end to engage the stent end, as shown in FIG. 6.

Figure 6:
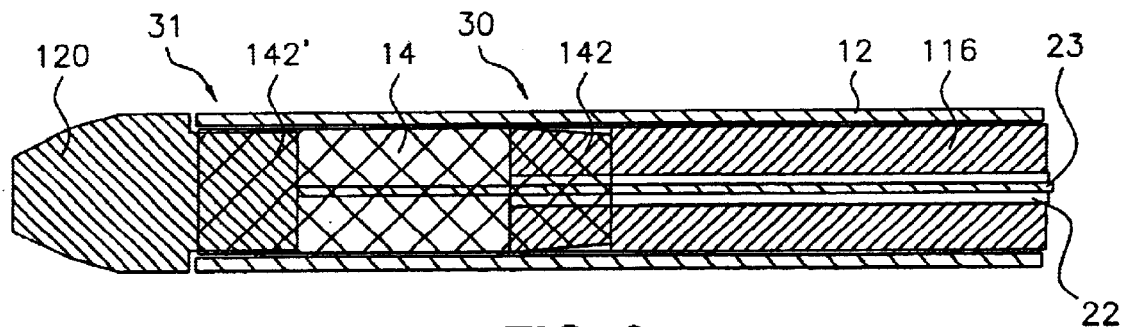
FIG. 6 a longitudinal section schematic illustration of exemplary docking sections of the present invention, showing the stent in a compressed state with a pusher docking section and a catheter docking section inserted in the ends thereof.

As shown in FIG. 6, docking section 142' of catheter tip 120 is a reduced diameter section (i.e., an insert) of catheter 120 that fits within distal end 31 of compressed stent 14. Docking section 142 of pusher 116 fits within proximal end 30 of compressed stent 14, and is radially biased outward to firmly hold stent 14 against sheath 12. Such bias outward to radially urge the stent proximal end 29 against the inner surface of the deployment sheath 12 further facilitates pusher 116 and stent 14 moving as one without pulling away from one another. Although docking section 142' having merely a reduced diameter section is illustrated in FIG. 6 with respect to catheter tip 120 whereas radially-biased-outward docking section 142 is illustrated with respect to pusher 116, either configuration is applicable to both the catheter tip and the pusher. As described above, however, a non-biased configuration is generally preferred at the catheter tip for ease of delivery system retraction.

Figure 7A:
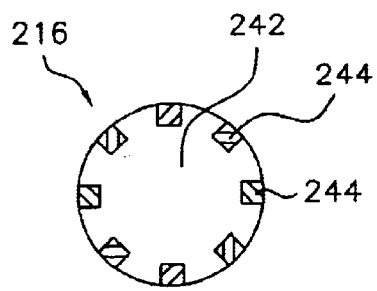
FIGS. 7A and 7B are an end view and a side view, respectively, of an exemplary docking section of the present invention comprising a set of fingers.
Figure 7B:
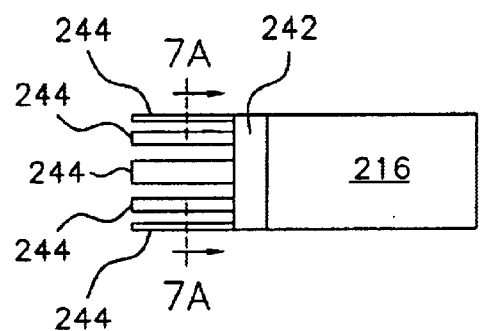
Figure 8A:
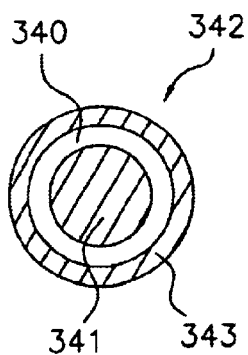
FIGS. 8A and 8B are an end view and a side view, respectively, of an exemplary docking section of the present invention comprising an annular pocket.
Figure 8B:
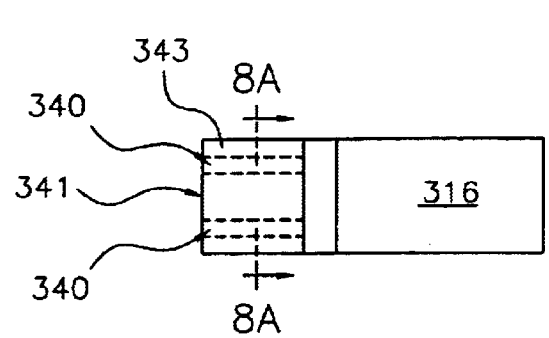
Figure 8C:
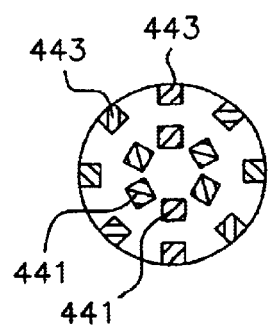
FIG. 8C is an end view of an exemplary docking section of the present invention, showing a docking section comprising an annular pocket defined by a plurality of fingers.

In another exemplary embodiment, shown in FIGS. 7A and 7B, docking section 242 of pusher 216 may comprise engagement means in the form of a set of fingers 244. Fingers 244 may define a pocket adapted for surrounding the stent, as shown in FIGS. 7A and 7B. Referring now to FIGS. 8A and 8B, in yet another embodiment, docking section 342 of pusher 316 may comprise pocket 340 in the form of an annular pocket between inner wall 341 and outer wall 343 adapted for insertion of the stent proximal end (not shown). Inner wall 341 may define a hollow or solid cylinder, or may be in the form of fingers that insert within the stent. Outer wall 343 may be solid as shown in FIGS. 8A and 8B, or may be in the form of outer fingers. As shown in FIG. 8C, another embodiment may comprise a plurality of inner fingers 441 and outer fingers 443 that define the inner wall and outer wall, respectively. Another embodiment, not shown, may comprise only inner fingers 441. Such inner fingers, outer fingers, or combination thereof may be radially biased outward. Although docking sections 242, 342, and 442 are described and shown in FIGS. 7A–8B with respect to pushers, similar docking section configurations may be provided for catheter tips.

The invention also comprises a method for pre-loading a stent delivery system, as described below relative to FIGS. 3 and 4. The method comprises loading at least compressed stent 14 and pusher 16' within outer sheath 12, including releasably engaging a portion of stent proximal end 30 with docking section 42 at pusher 16' distal end 28, stent distal end 31 with docking section 42' at catheter tip 20' proximal end 29, or a combination thereof. The method may include disposing a portion of the corresponding stent end 30 or 31 within a pocket 40 in docking section 42 or 42'.

Figure 5:
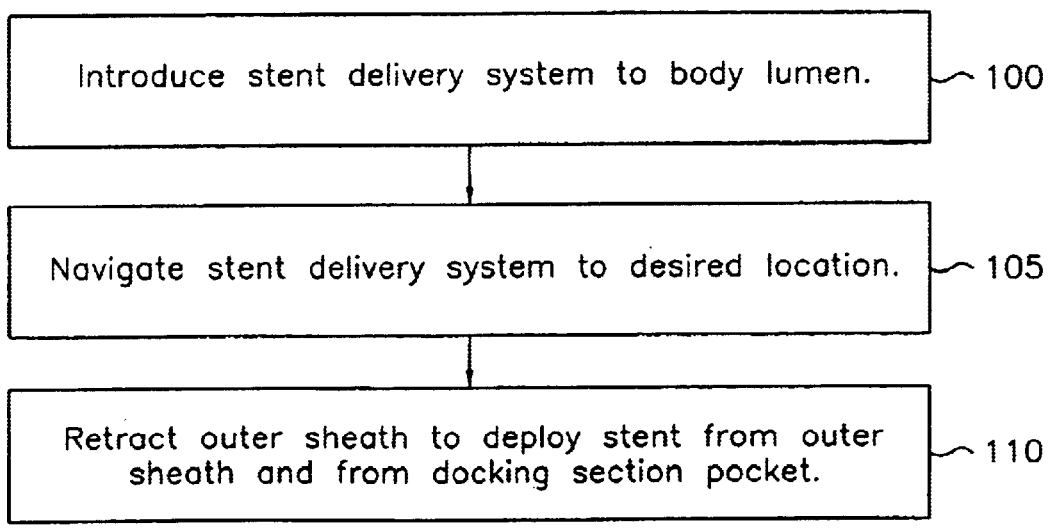
FIG. 5 is a flowchart depicting an exemplary method of deploying a stent in accordance with the present invention.

The invention further comprises a method for deploying a stent in accordance with the flowchart depicted in FIG. 5 and the drawings shown in FIGS. 3 and 4. The method comprises in step 100, introducing a pre-loaded stent delivery system 10' to a body lumen. Delivery system 10' comprises a compressed stent 14 having a proximal end 30 and a distal end 31, a pusher 16' having a distal end 28, a catheter tip 20' having a proximal end 29 and attached to a central core 23 slideably disposed within pusher 16'. At least one of pusher 16' or catheter tip 20' have a docking section 42 or 42' adapted to releasably engage the stent end over some length thereof, such as with pocket 40 and/or 40' within which the stent end is disposed. Outer sheath 12 overlies compressed stent 14, pusher 16', and each docking section 42 and/or 42'. Next, in step 105, the stent delivery system is navigated to a desired location for deploying stent 14, and finally, in step 110, outer sheath 12 is retracted to deploy the stent from the outer sheath and from docking section 42 and/or 42' into the desired location. Where catheter tip 20' has a docking section 42', the method may further comprise advancing central core 23 and the catheter tip 20' attached thereto prior to retracting sheath 12, to further facilitate release of stent 14 from the docking section. Where pocket 40 has an end rim 44 that is radially biased outward and adapted to be inwardly compressed to grip the stent end when loaded within outer sheath 12, as shown in FIGS. 3 and 4, the method may further comprise the end rim expanding outward during evacuation of the stent from the pocket. Where; as is shown in FIG. 6, docking section 142 and/or 142' comprise a reduced diameter section adapted for inserting within the end of stent 14, the method may further comprise the stent expanding away from the reduced diameter section.

While the present invention has been described with respect to specific embodiments thereof, it is not limited thereto. Therefore, the claims that follow are intended to be continued to encompass not only the specific embodiments described but also all modifications and variants thereof which embody the essential teaching thereof.

What is claimed:

1. A stent delivery system-adapted to deliver a compressed stent having a proximal end and a distal end to a distal deployment location inside a body lumen from a proximal access location outside the body lumen, the stent delivery system comprising:

a pusher having a distal end located adjacent the stent proximal end; and a catheter tip having a proximal end located adjacent the stent distal end and attached to a central core slideably disposed within the pusher;

wherein at least one of the pusher distal end and catheter tip proximal end comprises a docking section adapted to releasably engage a limited length of one end of the compressed stent, the docking section comprising an axially flared engagement surface which extends inside a short axial length of the stent.

2. The stent delivery system of claim 1 wherein the docking section comprises an inner set of fingers that extend inside a short axial length of the stent.

3. A pusher adapted to facilitate delivery of a compressed stent to a distal deployment location inside a body lumen from a proximal access location outside the body lumen, the pusher having a distal end comprising a docking section having a flared end rim with an inward protrusion that is radially biased outward relative to the compressed stent and adapted for the inward protrusion to releasably grip a limited length of a proximal end of the stent in pushing engagement therewith when the flared end rim is inwardly compressed to a non-flared diameter.

4. The pusher of claim 3 wherein the docking section is adapted to be inwardly compressed for insertion within a delivery sheath.

5. The pusher of claim 3 wherein the docking section comprises a pocket adapted to contain the stent proximal end inserted therein.

6. The pusher of claim 3 wherein the docking section is integral to the pusher.

7. The pusher of claim 3 wherein the docking section is an attachment to the pusher.

8. A pusher adapted to facilitate delivery of a compressed stent to a distal deployment location inside a body lumen from a proximal access location outside the body lumen, the pusher having a distal end comprising a docking section that is radially biased outward relative to the compressed stent and adapted to releasably engage a limited length of a proximal end of the stent in pushing engagement therewith, wherein the docking section comprises an insert comprising an axially flared engagement surface adapted to be inserted within the stent proximal end.

9. A catheter tip having a proximal end comprising a docking section adapted to releasably engage a limited length of a distal end of a compressed stent during delivery of the stent to a distal deployment location inside a body lumen from a proximal access location outside the body lumen wherein the docking section comprises an axially flared engagement surface comprising a reduced diameter section of the catheter tip that extends inside a short axial length of the stent.

10. A method for loading a stent delivery system adapted to deliver a compressed stent having a proximal end and a distal end to a distal deployment location inside a body lumen from a proximal access location outside the body lumen, the stent delivery system comprising a pusher having a distal end located adjacent the stent proximal end, and a catheter tip having a proximal end located adjacent the stent distal end and attached to a central core slideably disposed within the pusher; the method comprising:

loading at least the compressed stent and a pusher within an outer sheath, including releasably engaging a portion of one of: the stent proximal end with a pusher docking section that is radially biased outward relative to the compressed stent at the pusher distal end; the stent distal end with a catheter tip docking section; or a combination thereof, wherein at least one of the pusher docking section or the catheter tip docking section comprises (a) a flared end rim that is radially biased outward and adapted to be inwardly compressed, the docking section comprising a pocket having an inward protrusion that grips the stent when the docking section is loaded within the outer sheath, or (b) an axially flared engagement surface which extends inside a short axial length of the stent.

11. The method according to claim 10 wherein releasably engaging the portion of the stent proximal end with the docking section at the pusher comprises inserting the stent proximal end within the pocket in the docking section at the pusher.

12. The method according to claim 11 wherein releasably engaging the portion of the stent distal end with the catheter tip docking section comprises inserting the catheter tip docking section inside the stent distal end.

13. A method for deploying a stent in a distal deployment location inside a body lumen from a proximal access location outside the body lumen, the method comprising:

a) introducing a pre-loaded stent delivery system into the body lumen, the stent delivery system housing a compressed stent having a proximal end and a distal end and comprising a pusher having a distal end located adjacent the stent proximal end and a catheter tip having a proximal end located adjacent the stent distal end and attached to a central core slideably disposed within the pusher, one or both of the pusher distal end and catheter tip proximal end comprising a docking section that releasably engages a limited length of one end of the compressed stent, and an outer sheath overlying the compressed stent, the pusher, and each docking section, at least one of the pusher docking section or catheter tip docking sections comprising at least one of: an annular pocket having an inner wall and an outer wall, a pocket having a radial protrusion therein adapted to releasably secure the distal end of the stent within the pocket, or an axially flared engagement surface that extends inside a short axial length of the stent;

b) navigating the stent delivery system to a desired location for deploying the stent; and c) retracting the outer sheath to deploy the stent from the outer sheath into the desired location and to release the stent from each docking section.

14. The method of claim 13 wherein said at least one docking section comprises the pocket for receiving the stent end, and step (c) comprises evacuating the stent from the pocket.

15. The method of claim 14 wherein said at least one docking section pocket for receiving the stent end has an end rim that is radially biased outward and adapted to be inwardly compressed to grip the stent end when loaded within the outer sheath, and wherein step (c) further comprises the end rim expanding outward during evacuation of the stent from the pocket.

16. The method of claim 13 wherein said at least one docking section comprises a reduced diameter section adapted for inserting within the stent end, and step (c) comprises the stent expanding away from the reduced diameter section.

17. The method of claim 13 wherein the catheter tip comprises one of said docking sections and step (c) further comprises distally advancing the central core and the catheter tip attached thereto to further facilitate release of the stent from the catheter tip docking section.

18. A stent delivery system adapted to deliver a compressed stent from a proximal access location outside the body lumen to a distal deployment location inside a body lumen, the compressed stent having a proximal end and a distal end, the stent delivery system comprising at least one docking section defining a pocket adapted to releasably contain a limited length of one end of the compressed stent, the pocket comprising at least one of: (a) an annular pocket having an inner wall and an outer wall, and (b) a pocket having a radial protrusion therein adapted to releasably secure the distal end of the stent within the pocket.

19. The stent delivery system of claim 18 wherein the docking section includes a radiopaque marker.

20. The stent delivery system of claim 18 wherein the stent is a self-expanding stent.

21. The stent delivery system of claim 18 in which the pocket comprises a radially biased outward flared end rim having a first configuration in which the end rim has a flared diameter that is greater than a diameter of a remainder of the pocket, and a second configuration in which the end rim is radially compressed to a non-flared diameter that is equal to the diameter of the remainder of the pocket.

22. A method for loading a stent delivery system adapted to deliver a compressed stent from a proximal access location outside the body lumen to a distal deployment location inside a body lumen, the stent having a proximal end and a distal end, the stent delivery system comprising a pusher, a catheter tip attached to a central core slideably disposed within the pusher, at least one docking section defining a pocket adapted to releasably contain a limited length of one end of the compressed stent, and an outer sheath, the docking section pocket comprising at least one of: (a) an annular pocket having an inner wall and an outer wall, and (b) a pocket having a radial protrusion therein adapted to releasably secure the distal end of the stent within the pocket; the method comprising loading the compressed stent about the central core between the catheter tip and the pusher, inserting one of the ends of the stent in the pocket, and enclosing at least the stent, central core, pusher, and each docking section within the outer sheath.

23. A method for deploying a stent in a distal deployment location inside a body lumen from a proximal access location outside the body lumen, the stent having a distal end, a proximal end, a compressed configuration, and an expanded configuration, the method comprising:

a) introducing a pre-loaded stent delivery system into the body lumen, the stent delivery system housing the stent in the compressed configuration and comprising a pusher, a catheter tip attached to a central core slideably disposed within the pusher, at least one docking section defining a pocket that releasably contains one end of the compressed stent, and an outer sheath overlying the compressed stent, the pusher, and each docking section, the docking section pocket comprising at least one of: (i) an annular pocket having an inner wall and an outer wall, and (ii) a pocket having a radial protrusion therein adapted to releasably secure the distal end of the stent within the pocket;

b) navigating the stent delivery system to a desired location for deploying the stent;

c) retracting the outer sheath to deploy at least a portion of the stent in the expanded configuration in the deployment location; and d) releasing from each pocket the end of the stent contained in the pocket.

24. A stent delivery system adapted to deliver a compressed stent having a proximal end and a distal end to a distal deployment location inside a body lumen from a proximal access location outside the body lumen, the stent delivery system comprising:

a pusher having a distal end located adjacent the stent proximal end;

a catheter tip having a proximal end located adjacent the stent distal end and attached to a central core slideably disposed within the pusher, at least one of the pusher distal end and catheter tip proximal end comprising a docking section adapted to releasably engage a limited length of one end of the compressed stent; and wherein the docking section comprises a pocket having a radial protrusion therein adapted to releasably secure the stent end within the pocket.

25. A stent delivery system of claim 24 wherein the pocket in the docking section has a flared end rim, the flared end rim being radially biased outward and adapted to be inwardly compressed to grip the stent end when the docking section is loaded in an outer sheath.

26. The stent delivery system of claim 25 wherein the docking section has a bottle-neck geometry when the flared end rim is compressed.

27. The stent delivery system of claim 25 wherein the compressed stent is pinched inward by the flared end rim against the central core.

28. The stent delivery system of claim 25 wherein the docking section comprises a set of fingers.

29. The stent delivery system of claim 25 comprising a pusher docking section having the docking section with the flared end rim that is radially-biased outward and a catheter tip docking section without a radially-biased outward flared end rim.

30. A pusher having a distal end comprising a docking section adapted to releasably engage a limited length of a distal end of a compressed stent during delivery of the stent to a distal deployment location inside a body lumen from a proximal access location outside the body lumen, the docking section comprising a pocket having a radial protrusion therein adapted to releasably secure the proximal end of the stent within the pocket.

31. The pusher of claim 30, wherein the radial protrusion comprises an inward protrusion originating from an outer periphery of the pocket.

32. A catheter tip having a proximal end comprising a docking section adapted to releasably engage a limited length of a distal end of a compressed stent during delivery of the stent to a distal deployment location inside a body lumen from a proximal access location outside the body lumen, the docking section comprising a pocket having a radial protrusion therein adapted to releasably secure the distal end of the stent within the pocket.

33. The catheter tip of claim 32, wherein the radial protrusion comprises an inward protrusion originating from an outer periphery of the pocket.

34. The catheter tip of claim 32 wherein the docking section comprises a flared end rim that is radially biased outward and adapted to be inwardly compressed so that the inward protrusion grips the stent end when inserted within a delivery sheath.

35. The catheter tip of claim 34 wherein the docking section is integral to the catheter tip.

36. The catheter tip of claim 34 wherein the docking section is an attachment to the catheter tip.

* * * * *